(12) United States Patent
Iida et al.

(10) Patent No.: US 6,798,928 B2
(45) Date of Patent: Sep. 28, 2004

(54) IMAGE RECORDING APPARATUS

(75) Inventors: Toyoo Iida, Kyoto (JP); Masanori Sato, Kyoto (JP); Tomoki Ishizawa, Kyoto (JP); Toshimichi Masaki, Kyoto (JP)

(73) Assignee: Omron Corporation, Kyoto (JP)

( * ) Notice: Subject to any disclaimer, the term of this patent is extended or adjusted under 35 U.S.C. 154(b) by 580 days.

(21) Appl. No.: 09/809,082

(22) Filed: Mar. 16, 2001

(65) Prior Publication Data

US 2001/0022863 A1 Sep. 20, 2001

(30) Foreign Application Priority Data

Mar. 17, 2000 (JP) ........................................ 2000-076102

(51) Int. Cl.$^7$ ............................. G06K 9/54; G06K 9/00
(52) U.S. Cl. ..................................... 382/305; 382/141
(58) Field of Search .............................. 382/141–152, 382/181, 260, 295, 305, 302; 348/86, 92; 250/306

(56) References Cited

U.S. PATENT DOCUMENTS

| | | | | |
|---|---|---|---|---|
| 5,894,528 A | * | 4/1999 | Yasumi et al. | 382/302 |
| 6,072,900 A | * | 6/2000 | Chiu et al. | 382/149 |
| 6,169,282 B1 | * | 1/2001 | Maeda et al. | 250/310 |
| 6,259,474 B1 | * | 7/2001 | Sera | 348/82 |
| 6,333,992 B1 | * | 12/2001 | Yamamura et al. | 382/149 |
| 6,396,945 B1 | * | 5/2002 | Ishii | 382/149 |

* cited by examiner

*Primary Examiner*—Kanji Patel
(74) *Attorney, Agent, or Firm*—Foley & Lardner LLP

(57) ABSTRACT

An image recording apparatus for recording image data of an inspection object and inspection data corresponding to inspection results outputted at their own respective timings from an inspection apparatus which judges quality by an image recognition process is equipped with a temporary storage portion for temporarily storing the image data and the inspection data, a storage device, and a control portion for synchronizing the image data and the inspection data and storing the synchronized image data and inspection data in the storage device based on relative position data from a prescribed signal sent from the inspection apparatus, wherein the control portion accesses the temporary storage portion to acquire previous data for at least the prescribed signal.

6 Claims, 11 Drawing Sheets

Individual Inspection Results     Measurement Data

Individual Inspection Results

FIG.12
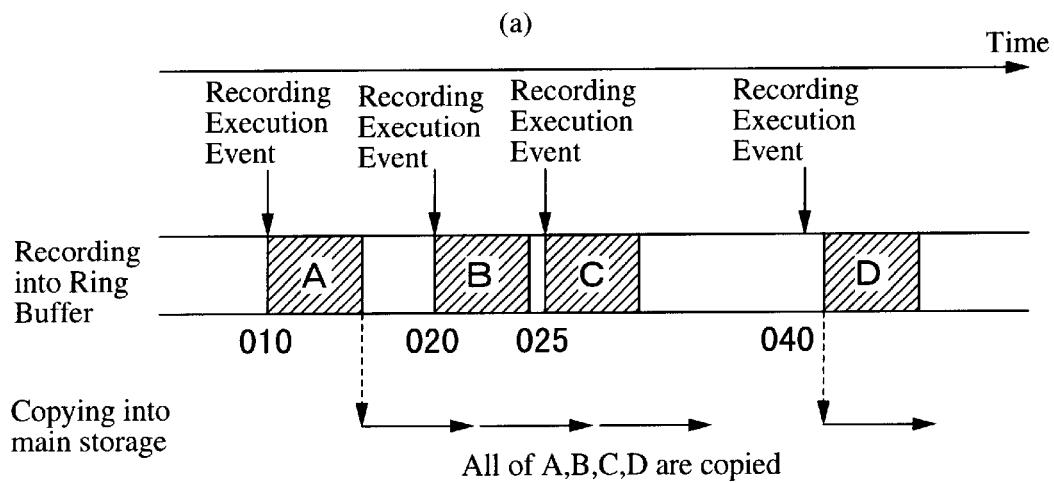
(a)
(b)
FIG.13
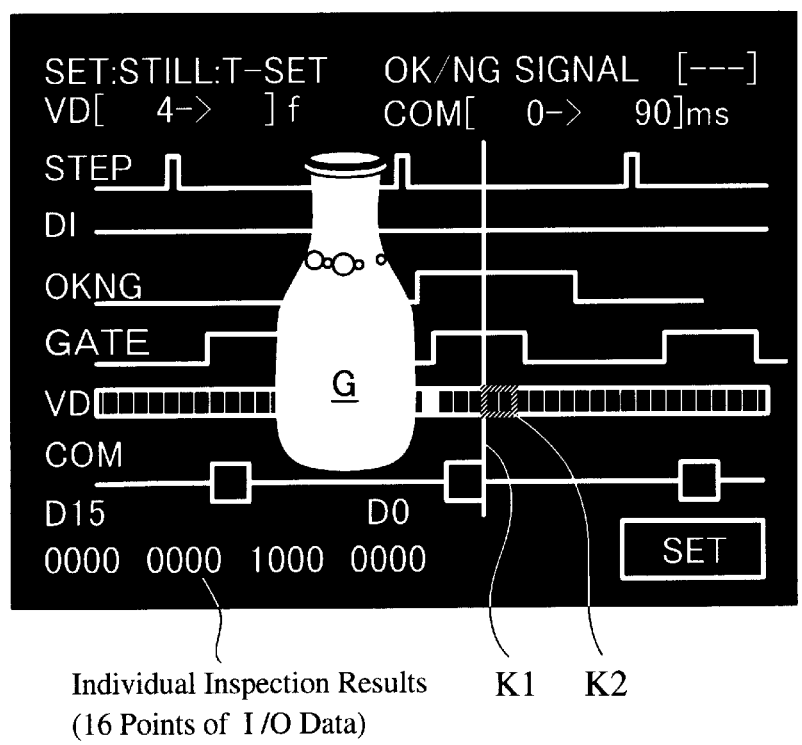

Odd-Numbered Field

Even-Numbered Field

Odd-Numbered Field

Even-Numbered Field

IMAGE RECORDING APPARATUS

FIELD OF THE INVENTION

The present invention relates to an image recording apparatus.

BACKGROUND OF THE INVENTION

In one example of a prior art quality control system for a factory production line (manufacturing process), a visual sensor is arranged at a prescribed position of the production line to pick up images of the products conveyed on such production line, and then an image recognition process is carried out based on the image data picked up by the visual sensor to judge whether or not the imaged product is a conforming product. Then, in the case where the imaged product is judged to be a nonconforming product, such product is discarded. In this way, only conforming products are shipped out, and this makes it possible to guarantee the quality of the products.

On the other hand, in recent years, in the quality control and quality maintenance of the manufacturing process, attention has shifted from discarding nonconforming products that have been previously detected in a reliable manner to suppressing the generation of such nonconforming products. In order to do this, the cause of the generation of nonconforming products has to be identified, and then appropriate improvements to the production equipment need to be carried out. However, in the prior art system described above, even though it is possible to detect the generation of nonconforming products, it is difficult to identify the cause of the generation of such nonconforming products.

Namely, current visual sensors have a function to preserve image data used for inspection. However, the number of frames that can be recorded is small, and because the system is established only with a function to simply store images, it becomes difficult to accurately identify the cause of the generation of nonconforming products only by looking at the images used for inspection.

Further, in another prior art system, images that form inspection objects are outputted from a visual sensor and stored in an external image recording device. At such time, it is possible to also output inspection results from the I/O output of the visual sensor. Preferably, such I/O output (inspection results) is also stored in the image recording device in order to increase the data available for investigating the cause of the generation of nonconforming products.

However, because the I/O output and the image data are not obtained simultaneously in the visual sensor, they are outputted at their own respective timings. Accordingly, in the case where I/O data based on the generation of a nonconforming product is acquired, there is the case where the image data of such imaged nonconforming product has already been passed, or the reverse case where the image data has not been received yet. In other words, when the nonconforming product number is received, there are cases where the displayed image is an image having no relation to such nonconforming product. Accordingly, because the contact output of the I/O can not be stored in connection with the image data, it is not possible to effectively utilize such data, and this makes it difficult to identify the cause of the generation of nonconforming products.

In order to overcome this problem, a system has been developed in which a time stamp is added to each outputted data, and based on such time stamps at the time the outputs are played back, the system recognizes the time when each data was generated, and by carrying out control to match such data, synchronization can be carried out. However, adding a time stamp to each data makes the system complex and requires a large memory capacity, and if the tact number (the number of processes carried out per unit time) in the production line is increased, the amount of data processed per unit time will also increase. Consequently, the timing matching process based on the time stamps will not be able to keep up with all the data that needs to be processed, and this makes it impossible to carry out a playback process that achieves synchronization.

SUMMARY OF THE INVENTION

It is an object of the present invention to provide an image recording apparatus which makes it possible to connect and store related data (image data, inspection data corresponding to inspection results) for identifying the cause of the generation of nonconforming products.

The image recording apparatus according to the present invention is an apparatus for recording image data of an inspection object and inspection data corresponding to inspection results outputted at their own respective timings from an inspection device which judges quality by an image recognition process, and includes a temporary storage portion for temporarily storing the image data and the inspection data, storage means, and control means for synchronizing the image data and the inspection data and storing the synchronized image data and inspection data in the storage means based on relative position data from the prescribed signal sent from the inspection device, wherein the control means accesses the temporary storage portion to acquire previous data for at least the prescribed signal.

In this way, because synchronization of the image data and the inspection data can be achieved from shift amounts based on relative position data from the prescribed signal sent from the inspection device, there is no need for each data to hold time stamps, and this makes it possible to carry out high-speed processes. In this connection, the inspection data corresponding to the inspection results is data related to the inspection results, and in the embodiments of the present invention, this data corresponds to individual inspection results, measurement data and the like. Further, the prescribed signal sent from the inspection device is a characteristic signal of the inspection device which forms a reference signal, and in the embodiments of the present invention, this signal is a GATE signal, but it is also possible to use the step signal which forms the source of the GATE signal. Of course, other signals may be used so long as they can form a reference for obtaining relative position data.

Further, the storage means may be provided internally in the image recording apparatus, or the storage means may be an external storage means. Further, in the embodiments of the present invention, the inspection device corresponds to the visual sensor, the temporary storage portion corresponds to the ring buffer provided in the main memory, and the storage means corresponds to the storage device.

Now, in case where a new recording execution event occurs while data is being stored in the storage means, it is possible to omit the recording of the image data and store only the inspection data. In this way, it is possible to reliably store inspection data even when the speed at which data is written into the storage means is slow, for example.

Further, the image recording apparatus includes a display means, wherein a timing chart showing at least the timing of the acquired fields is displayed by the display means based on data stored in the temporary storage portion, wherein a prescribed position of the displayed timing chart is designated, and image data based on the designated position is displayed on the display means independently or overlaid on the timing chart, and wherein the control means is equipped with an initialization function to establish relative position data from the prescribed signal at the time when image data is being stored in the storage means based on the reception of an input which determines whether or not the displayed image should be stored in the storage means. In this way, because the relative position can be obtained visually, initialization can be carried out easily.

Further, the designation of the timing chart can be changed to field units. In this way, even in the case of a system where the images are inputted into the image recording apparatus by appropriately switching between signals from a plurality of imaging means, by carrying out a frame-by-frame transmission in field units, it is possible to reliably identify the switching timing position, and this makes it possible to accurately determine the relative position data.

Now, it should be noted that the structural elements of the present invention described above can be combined in any possible way. Further, each of the means used to construct the image recording apparatus according to the present invention can be achieved by exclusive hardware circuits or by a programmed computer.

BRIEF DESCRIPTION OF THE DRAWINGS

FIG. 12 is a diagram for describing the operation of writing data into the storage device.

FIG. 13 is an example of an initialization screen for describing the initialization function.

DETAILED DESCRIPTION OF THE PREFERRED EMBODIMENTS

Figure 1:
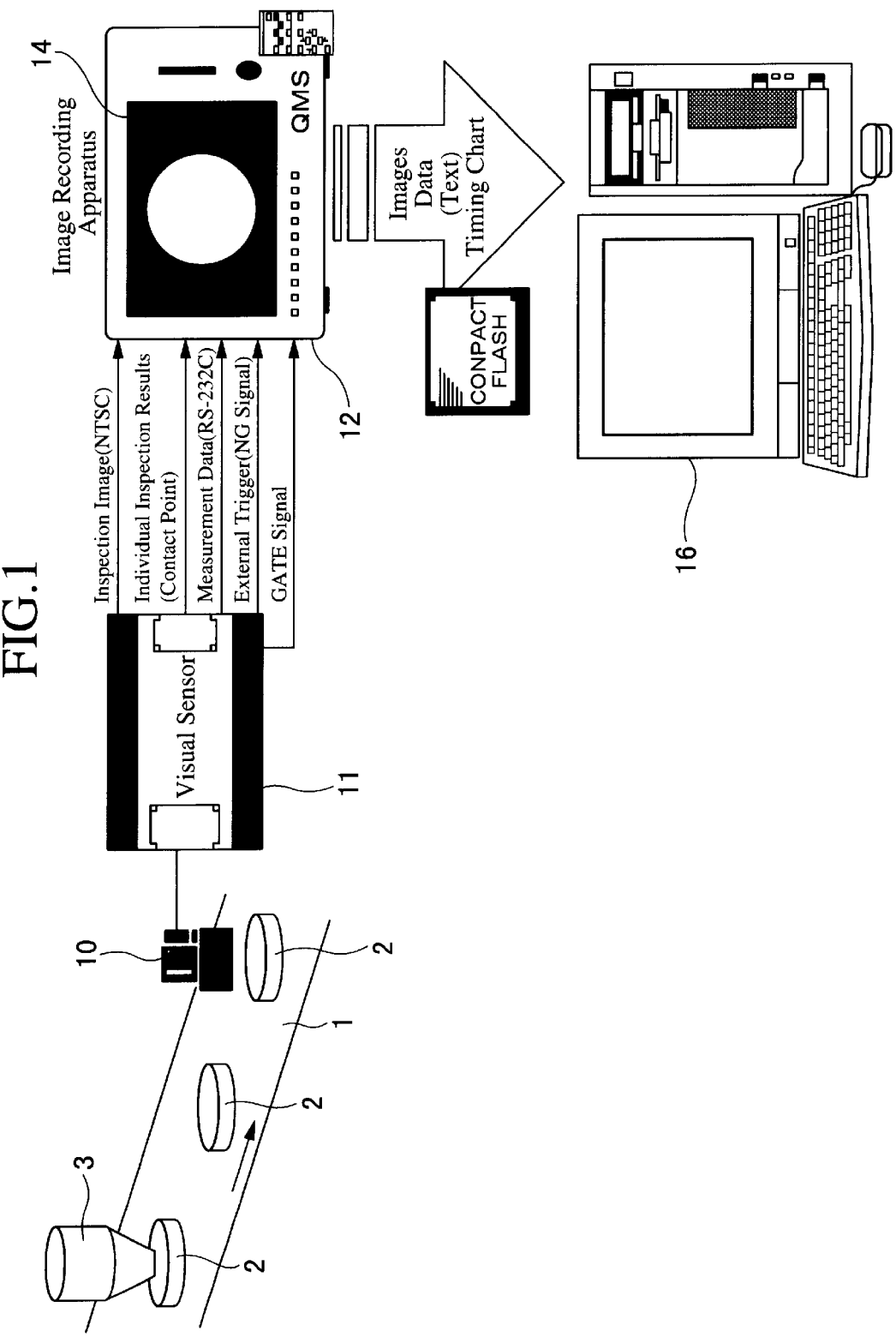
FIG. 1 shows an example of a production line in which the present invention is applied.
Figure 2:
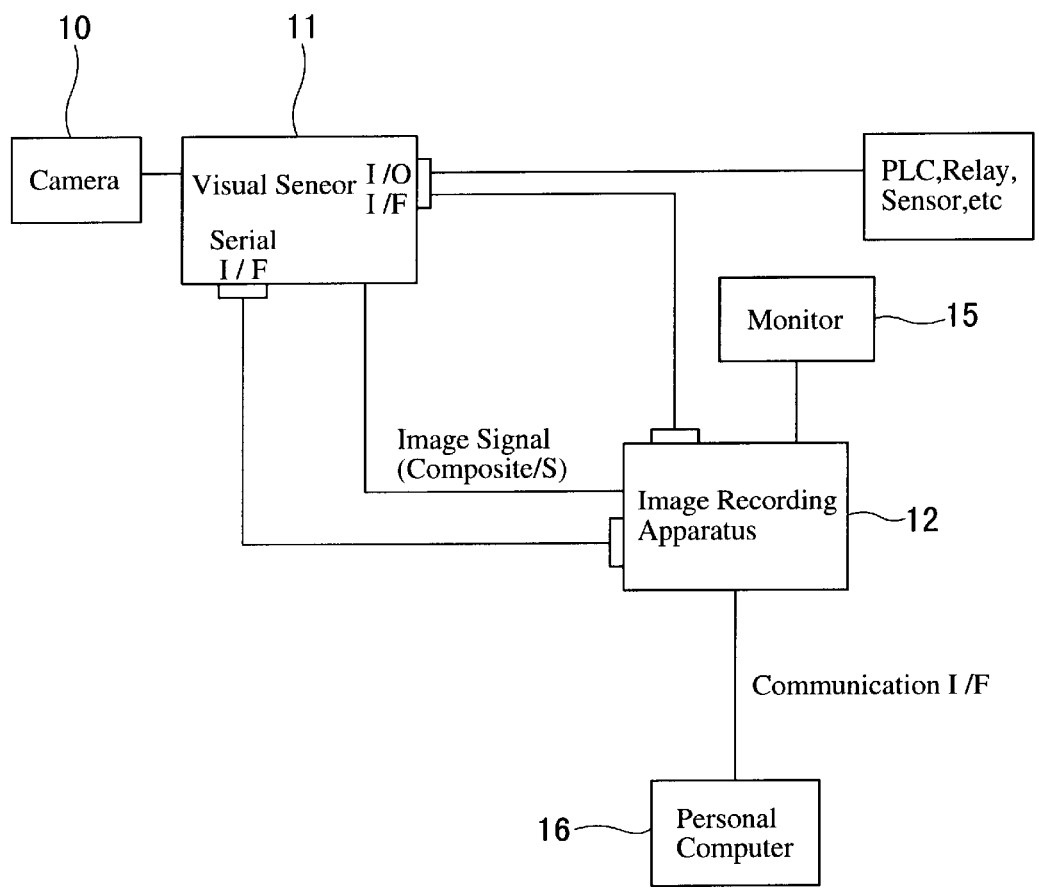
FIG. 2 is a block diagram showing an example of a system in which the present invention is applied.

FIGS. 1 and 2 show one example of system in which the present invention is applied. As shown in these drawings, articles 2 which form process objects (i.e., objects that will be processed) are placed on a conveyer 1 at prescribed spacings, and in this state the articles 2 are conveyed by the conveyor 1. These articles 2 undergo a prescribed process by manufacturing equipment 3 provided at a prescribed position of the conveyor 1.

In this production line, a camera 10 for taking images of the articles 2 is arranged above the conveyor 1 in the same manner as is done in the prior art, and the images (which form inspection objects) of the articles 2 taken by the camera 10 are sent as image data to a visual sensor 11. Then, in the visual sensor 11, a prescribed image recognition process is carried out on the image data of the imaged article 2 to judge whether a defect is present or absent, and in the case where a defect is present, a NG signal is outputted.

This NG signal is sent to an image recording apparatus 12 according to the present invention. Further, in addition to such NG signal, information used when judging the presence or absence of defects is sent as individual inspection results to the image recording apparatus 12. Namely, in the present embodiment, inspection object images are divided into 4×4 local regions, for example, and an image process such as matching with a reference pattern or the like is carried out for each of such local regions, wherein a judgement of quality is carried out for each local region. Then, in the case where at least one local region is not suitable, the article 2 under inspection is judged to be a nonconforming article, and then a NG signal (external trigger signal) is outputted. Then, the judgement results for each local region (for a total of 16 regions) undergo I/O data output as individual inspection results. Further, the characteristic quantity of image data (area, center, etc.) of the inspection object is calculated, and this calculated value is sent as measurement data to the image recording apparatus 12 via a RS-232C.

Furthermore, the inspected image data is outputted as a NTSC (National Television System Committee) signal for each field. Further, the visual sensor 11 also outputs a GATE signal which is a special signal that indicates the visual sensor 11 is able to read out the outputted I/O data.

Then, the NG signal, individual inspection results, image data, measurement data and GATE signal are outputted at their respective timings and sent to the image recording apparatus 12. Next, the image recording apparatus 12 synchronizes and records the acquired individual inspection results, image data and measurement data. This synchronization is carried out based on the GATE signal and the NG signal, and a detailed description thereof is given below.

In this connection, the image recording apparatus 12 is equipped with an internal display device 14 and is connected to an external monitor 15 to make it possible to display each of the acquired data. Further, the image recording apparatus 12 is connected to a personal computer 16 via a prescribed network, communication cable or the like to make it possible for the image recording apparatus 12 to transfer recorded results and the like.

Figure 3:
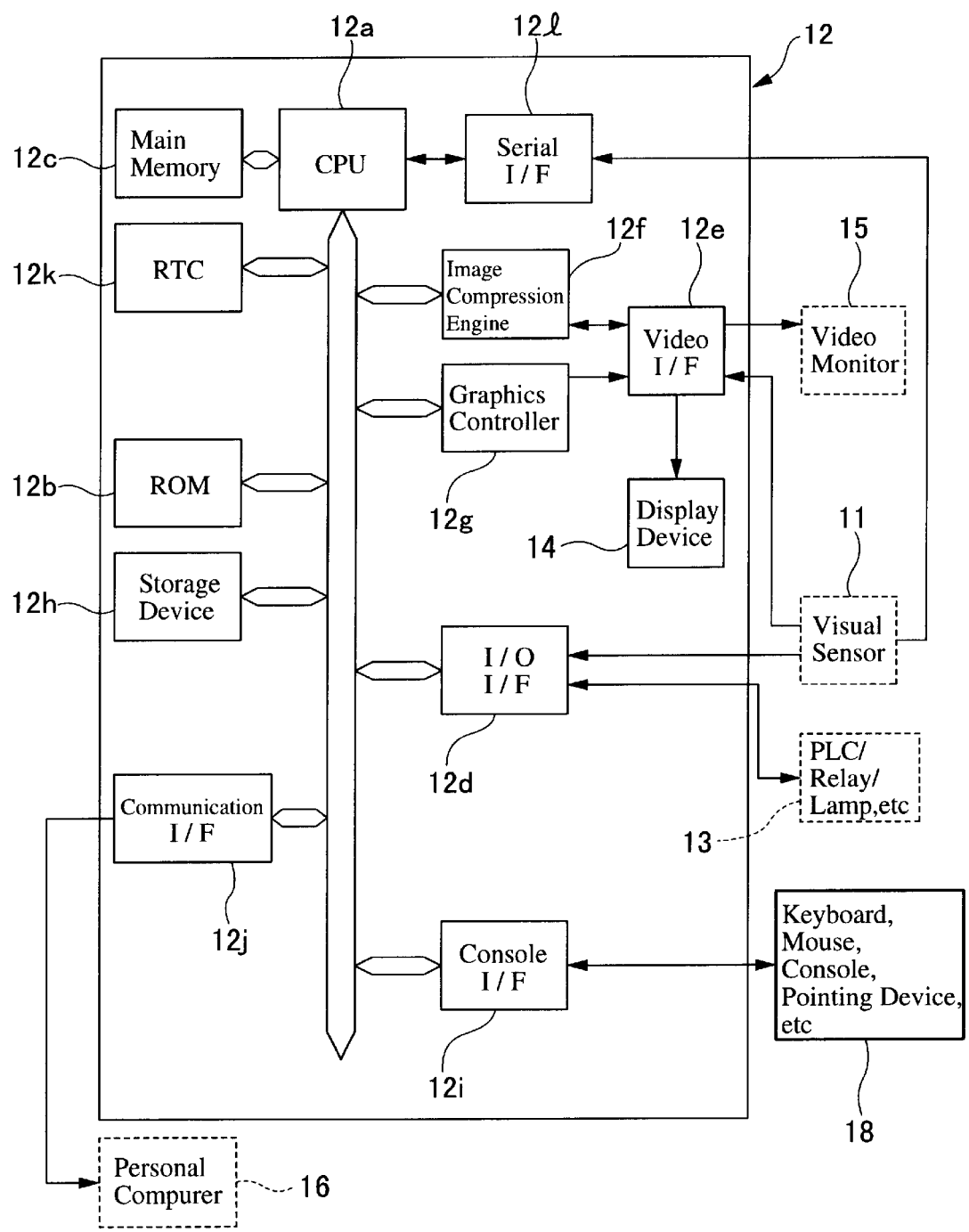
FIG. 3 shows an embodiment of the image recording apparatus according to the present invention.

Next, FIG. 3 shows an example of an actual internal structure of the image recording apparatus 12 having the functions described above. First, the image recording apparatus 12 is equipped with a CPU 12a made from a chip microcomputer. While making suitable use of a main memory 12c, this CPU 12a carries out prescribed processes and the like related to the present invention based on process programs, parameters and the like stored in a ROM 12b. In this regard, the actual process method will be described below. Further, the ROM 12b is constructed from a nonvolatile memory such as a EPROM, DTPROM or the like.

Then, the NG signal from the visual sensor 11 is sent to the CPU 12a via an I/O interface 12d. Namely, the I/O interface 12d is a multiple contact I/O interface equipped with a function to read in ON/OFF signals from the outside, and output ON/OFF signals to the outside. Accordingly, by connecting the visual sensor 11 to the I/O interface 12d, it is possible to acquire the NG signal, the individual inspection results and the GATE signal as ON/OFF signals. Further, by connecting devices 13 such as a PLC, relay, lamp and the like to the I/O interface 12d, it is possible to send ON/OFF control commands to such devices. These control commands are also sent out from the CPU 12a. Further, it is possible to also acquire the data outputted from each type of device 13. Furthermore, the measurement data from the visual sensor 11 is acquired by the CPU 12a via a serial interface 12l.

Further, the image signal (still image) from the visual sensor 11 is acquired internally via a video interface 12e. Namely, the video interface 12e carries out an A/D conversion to convert the analog image signal sent from the visual sensor 11 to a digital image signal, and then the digital image signal is transferred to an image compression engine 12f.

The image compression engine 12f carries out real-time compression/expansion of the acquired image data for each field unit. Accordingly, the digital converted image data received from the video interface 12e is compressed and then sent to the CPU 12a. Further, the image data for output display acquired from the CPU 12a and the like is expanded by the image compression engine 12f and then transferred to the video interface 12e.

Then, because the video interface 12e is connected to the internal display device 14 and the external monitor 15, the expanded image is outputted and displayed on the display device 14 and/or the external monitor 15.

Further, a graphics controller 12g is connected to the video interface 12e, and the menu, characters, lines and the like created by the graphics controller 12g are acquired and displayed on the internal display device 14 and the external monitor 15.

Furthermore, the image recording apparatus 12 is also equipped with a storage device 12h which is a nonvolatile memory for storing recorded data and a portion of the system program; a console interface 12i which receives data from and transmits data to a connected pointing device 18 such as a keyboard, mouse, console unit or the like for controlling the image recording apparatus 12; a communication interface 12j for making a connection to an Ethernet or the like; and a real time clock (RTC) 12k for controlling the clock (year, month, day, hour, minute, second) inside the system. In this regard, because each of these devices has the same basic hardware structure as those devices from the prior art, a detailed description of such devices is omitted.

Figure 4:
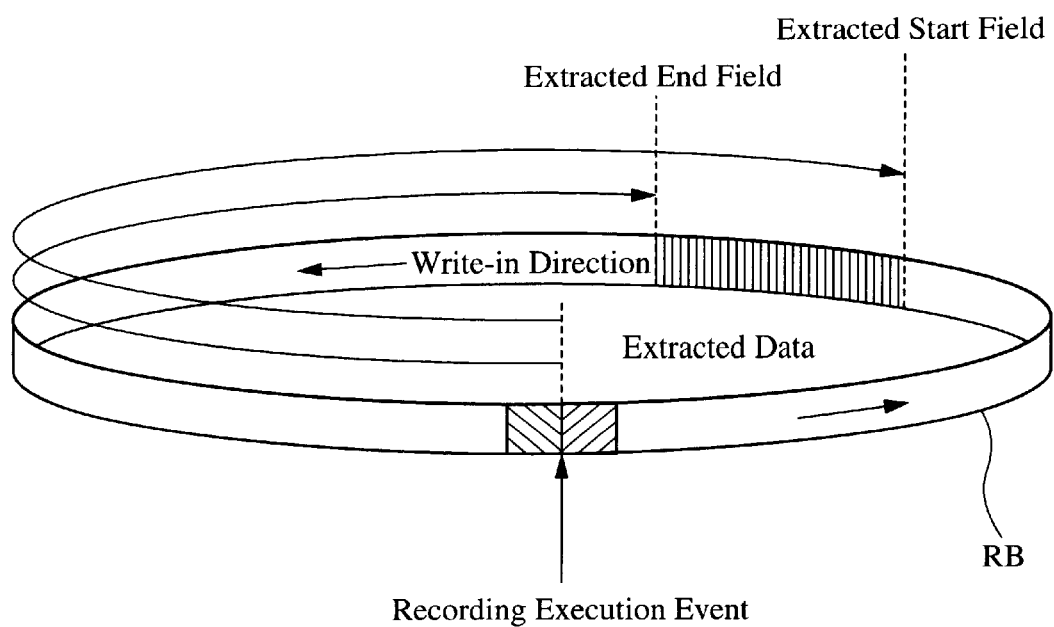
FIG. 4 is an illustration for describing the ring buffer and usage state thereof.

Now, in the present invention, the CPU 12a forms a ring-shaped buffer (ring buffer) RB on the main memory 12c as shown in FIG. 4, and the CPU 12a writes acquired data into this ring buffer RB in order to temporarily preserve such data. Further, required portions of such temporarily preserved data are read out and then written into the storage device 12h. The reading and writing of such data is a function of the CPU 12a. Further, instead of writing data into the storage device in such manner, it is also possible to transfer the data to the personal computer 16 via the communication interface 12j. Further, the data stored in the storage device 12h can be sent to the personal computer 16.

In this regard, the memory capacity of the ring buffer RB is established to make it possible to store a Tmax (in seconds) portion image data and information related thereto. Furthermore, because the data written into the main memory 12c is in the form of three types of data, namely, image data, serial data (measurement data) and I/O data (individual inspection results), individual ring buffers may be prepared for respectively storing each of such three types of data, or a plurality of such data may be stored in a single ring buffer.

Furthermore, when a recording execution event does not occur, after Tmax, the formed ring buffer RB becomes full with data stored therein. Accordingly, in the case where an image is subsequently acquired, such acquired image data is first written and preserved in a region where image data is stored. In this way, from the beginning of recording until after Tmax, the image and other related data during the previous Tmax interval are kept in a temporarily preserved state in the ring buffer RB.

Then, when reading out from the ring buffer RB, such reading operation is carried out in a manner the synchronizes each data. In this way, because synchronization can be obtained for each type of data stored in the storage device 12h, in the case where thereafter the data stored in the storage device 12h is played back and displayed on the display device 14 and the external monitor 15, because data related to a defective article is outputted and displayed, the cause of such defect can be easily investigated.

Figure 5:
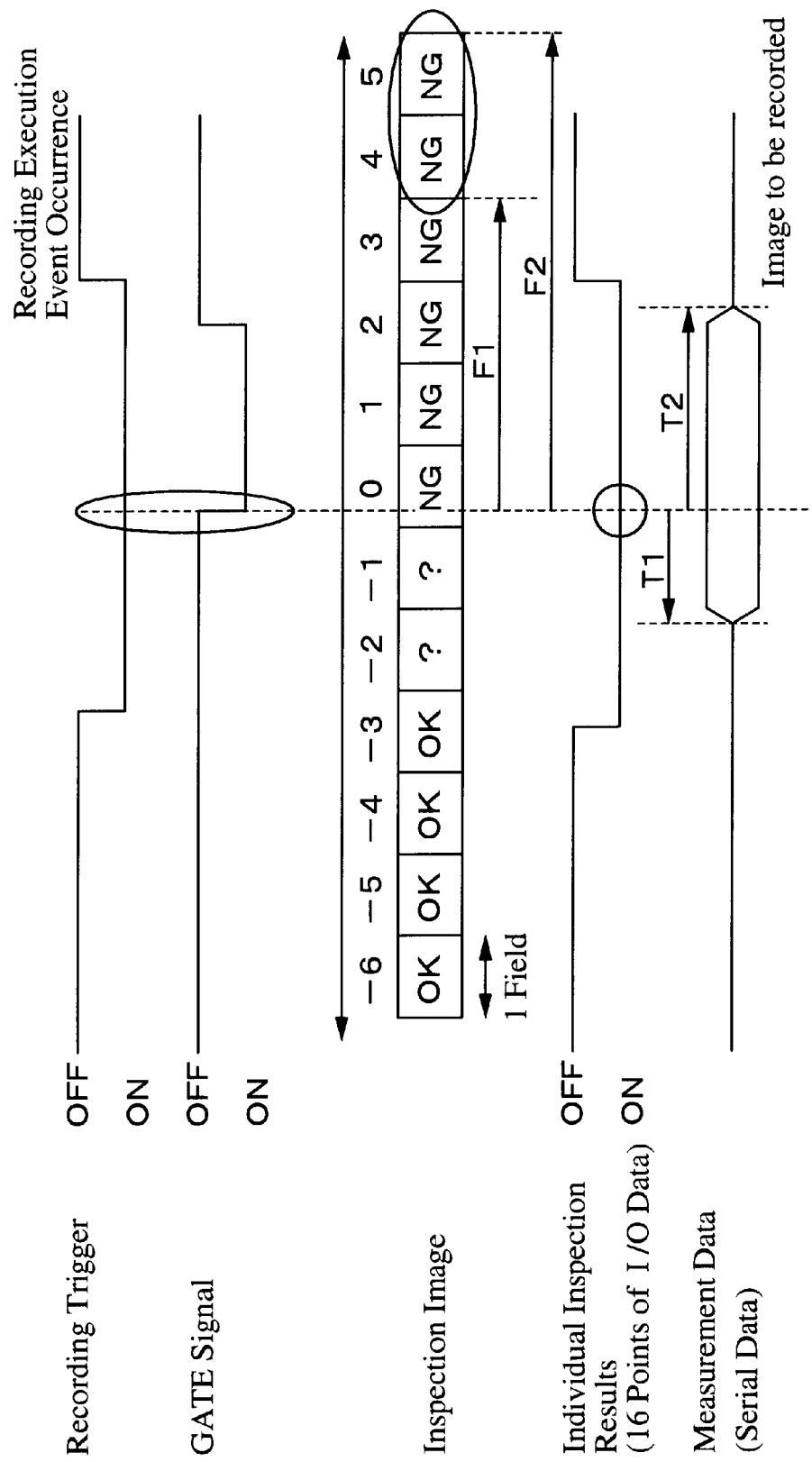
FIG. 5 shows an example of a timing chart for each signal.

Next, the method of obtaining synchronization will be described. In this connection, FIG. 5 is a timing diagram showing the output state of the recording trigger (Low NG signal ON), GATE signal, inspection image (where one frame represents one field), individual inspection results and measurement data. In this example, O is established for the time when the GATE signal goes into an ON state (from High to Low), and a time series is expressed by field units. In this regard, all the ON/OFF signals in this example are ON for the Low state. Further, the inspection image is "NG" in the case where the inspection results indicate a nonconforming article, "OK" in the case of a conforming article, and "?" when a judgement is not possible, such as in the case where a judgement object image is not present inside the inspection region.

Further, each of the signals described above is outputted at their own respective timing without being mutually synchronized with the other signals, and each signal is outputted at a fixed timing. Moreover, the sequential relationship of the data outputted at the same point in time is not clear. Namely, there are cases where the inspection images are outputted after the GATE signal has been generated, and there are cases where the inspection images are outputted before the GATE signal is generated. This same problem also occurs between other signals. Further, in the sequential relationship of the actual process, for example, because a recognition process and article quality judgement are carried out after the inspection image is taken, the imaging process for the image data is faster than the output of the inspection results, and when data is actually outputted to the outside, various processes are carried out, but due to such factors as the relationship of the data capacity and the like, the output order and the order in which the actual processes are carried out do not necessarily match.

As described above, because each signal is outputted without obtaining synchronization, each signal is outputted at their own respective fixed timing. Accordingly, if the gate signal is considered as a reference, for example, the desired field storing the image data and the relative position of the measurement data are known. Consequently, by accessing the ring buffer RB based on related relative position data to obtain the field and data in such relative position relationship, it is possible to achieve synchronization.

Specifically, in the present embodiment, when the recording trigger and the GATE signal are both in an ON state, an event is generated. Then, when this event is generated, the data in a prescribed relative position relationship based thereon is read out from the ring buffer RB and the like. For example, if the inspection image data at the point in time where the recording trigger and the GATE signal both reach an ON state is assigned the reference position field (0), the head field and the end field of the image to be recorded can be stipulated by relative field numbers with respect to the reference field. In the example shown in FIG. 5, the head field is the F1'th field, namely, the 4'th field after the GATE signal is generated, and the end field is the F2'th field, namely, the S'th field after the GATE signal is generated.

Similarly, the measurement data specifies the head position F1 and the end position F2 by the relative time interval from the reference position (the point in time where the trigger signal and the GATE signal both reach an ON state). In the example shown in FIG. 5, F1 has a negative value, and data is acquired by returning to past information. Further, the individual inspection results acquire the reference position value as effective data. Namely, in the present embodiment, by using the ring buffer RB, because past data is also stored and preserved, it becomes possible to acquire desired data even when such data is past data. Of course, when the desired data is future data, such data can be stored temporarily without alteration in the ring buffer RB in accordance with the data collection from the visual sensor 11, and when arriving by such timing, this data can be acquired.

Further, in the example shown in FIG. 5, only T1 has a negative value while the other ones have positive values, but if T1, F1 came later in time than T2, F2, it does not matter which value is positive or negative.

Figure 6:
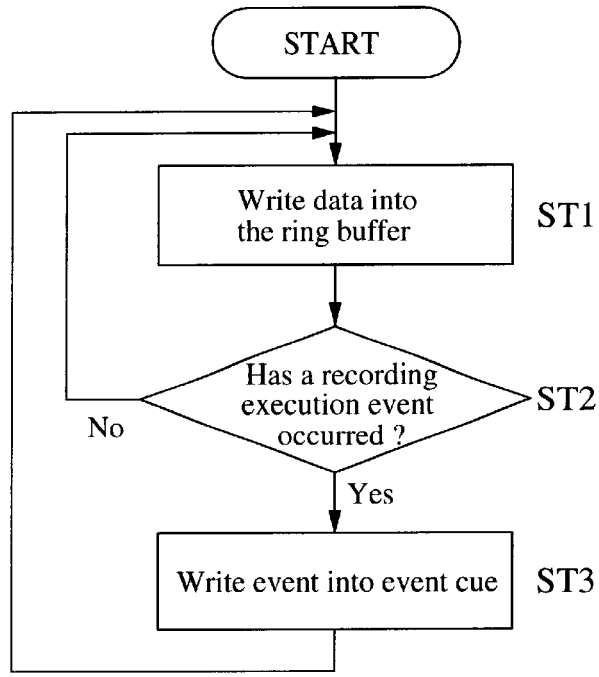
FIG. 6 is a flow chart for describing the function of the CPU.

Next, the function of the CPU 12a will be described. First, by means of a prescribed initialization carried out as a prerequisite, the CPU 12a is designed to know the relative position data for acquiring each data based on the reference position described above (recording execution event occurrence: recording trigger, GATE signal and the like are ON). At the beginning of this prerequisite, the CPU 12a executes the flow chart shown in FIG. 6.

First, the still image data (each field) sent sequentially from the image recording apparatus 12 is compressed by the image compression engine 12f, and such compressed data is sequentially written into the ring buffer RB from the head thereof. At this time, time data from the real time clock 12k is read out, and then the time (time stamp) each image is recorded and the record number (consecutive number from the point in time where recording is started) are connected and stored sequentially (ST1).

Next, a judgement of whether or not a recording execution event occurred is carried out (ST2), and in the case where an event does not occur, the process returns to Step 1, and the writing in of the next image data (field) is carried out. The judgement of whether or not an event occurred is carried out by monitoring the received GATE signal and recording trigger, wherein a recording execution event is judged to occur when both the GATE signal and the recording trigger are ON at the same time.

On the other hand, in the case where a recording execution event occurs, after writing the event in the event cue (5T3), the process returns to Step 1. In this way, it is possible to return to only the previous Tmax portion in the main memory 12c.

Figure 7:
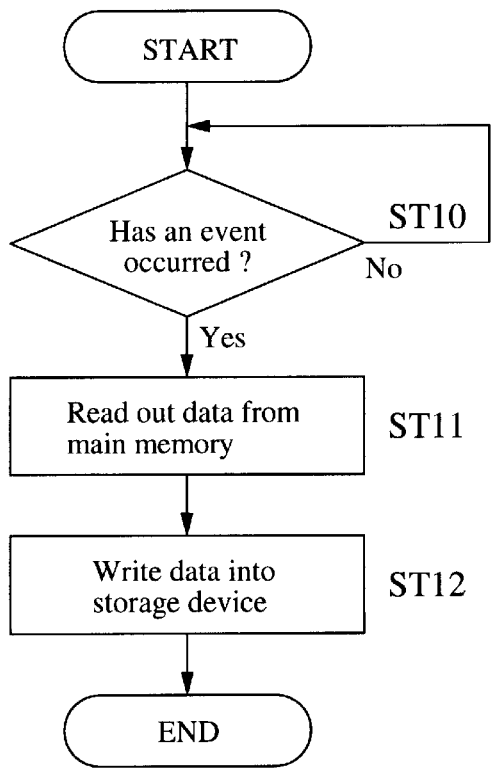
FIG. 7 is a flow chart for describing the function of the CPU.

Further, the process function for reading out data from the ring buffer RB and writing data into the storage device 12h executes the flow chart shown in FIG. 7. First, the system waits for an event to occur (ST10), and when an event occurs, the image data, measurement data and individual inspection results of the address corresponding to such event are read out from the ring buffer RB and written into the storage device 12h (ST11, ST12). In this regard, the "address corresponding to such event" is an address stipulated by a relative position from a reference position predetermined by initialization. Further, if the event occurrence time point is made the reference position, the individual inspection results are data written in at this same time point, and the measurement data is data written in at a later position separated by only a relative time (T1, T2) from this reference position. Furthermore, if the field at the reference position is made the reference field, then the image data is the field specified by relative field numbers (F1, F2) with respect to this reference field.

Incidentally, while data is being written in based on some recording execution event, there are times when the next recording execution event will occur. In this case, because each data is stored in the ring buffer RB, after the current process for storing data in the storage device 12h finished, a data storing process is carried out based on the next recording execution event.

However, when such recording execution events occur in succession, in the case where a slow-speed storage device such as a flash memory or the like is used as the storage device 12h, while waiting for data to be written in, there is the risk that the data which is waiting to be written in will be erased by new data written over the original ring buffer RB, thereby making it impossible to preserve data.

Figure 8:
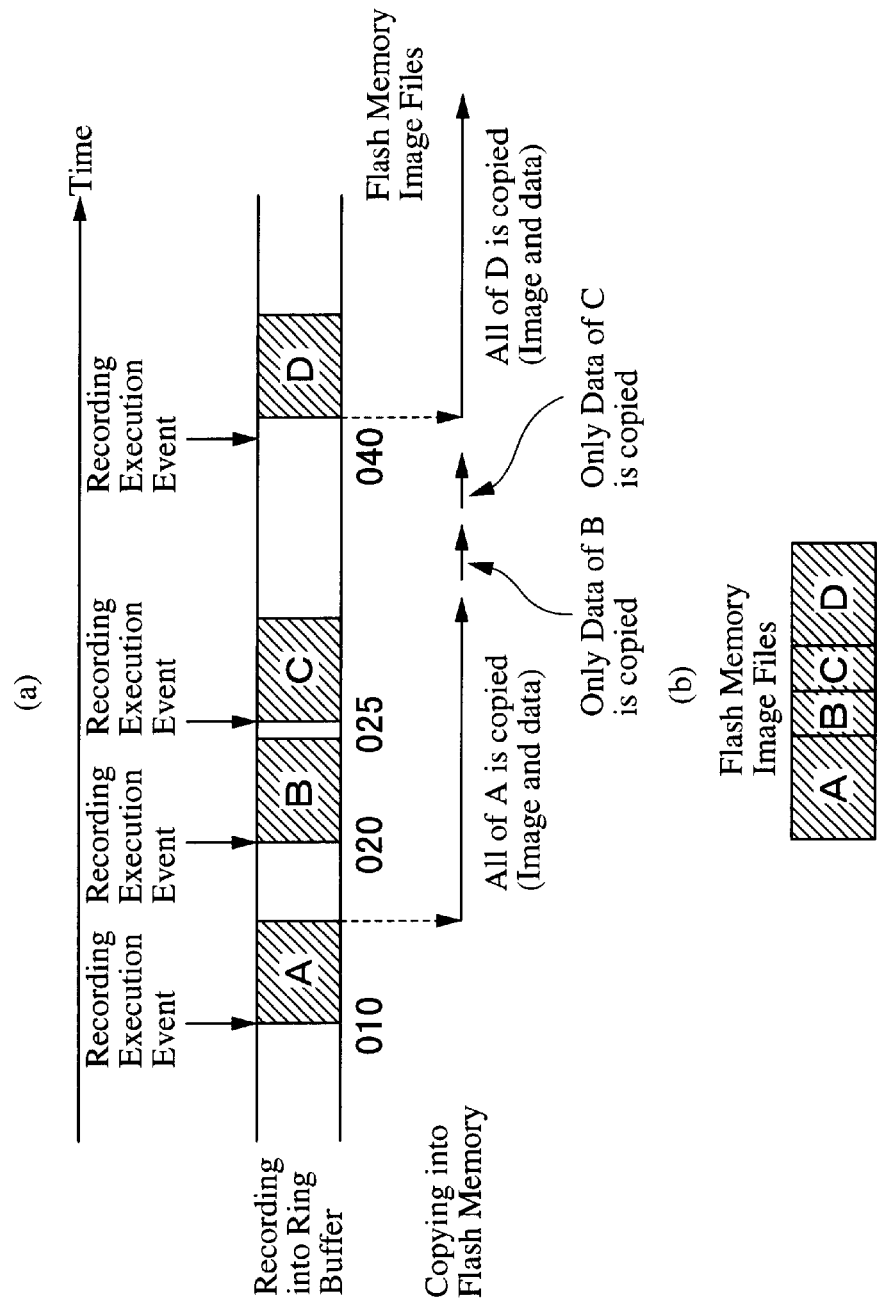
FIG. 8 is a diagram for describing the operation of writing data into the storage device.

In this regard, as shown in FIG. 8, in the case where recording execution events occur in succession, instead of writing in the image data which would require too much time to carry out due to the large amount of data involved, the images are omitted and only data (measurement data, individual inspection results data) are preserved.

Figure 9:
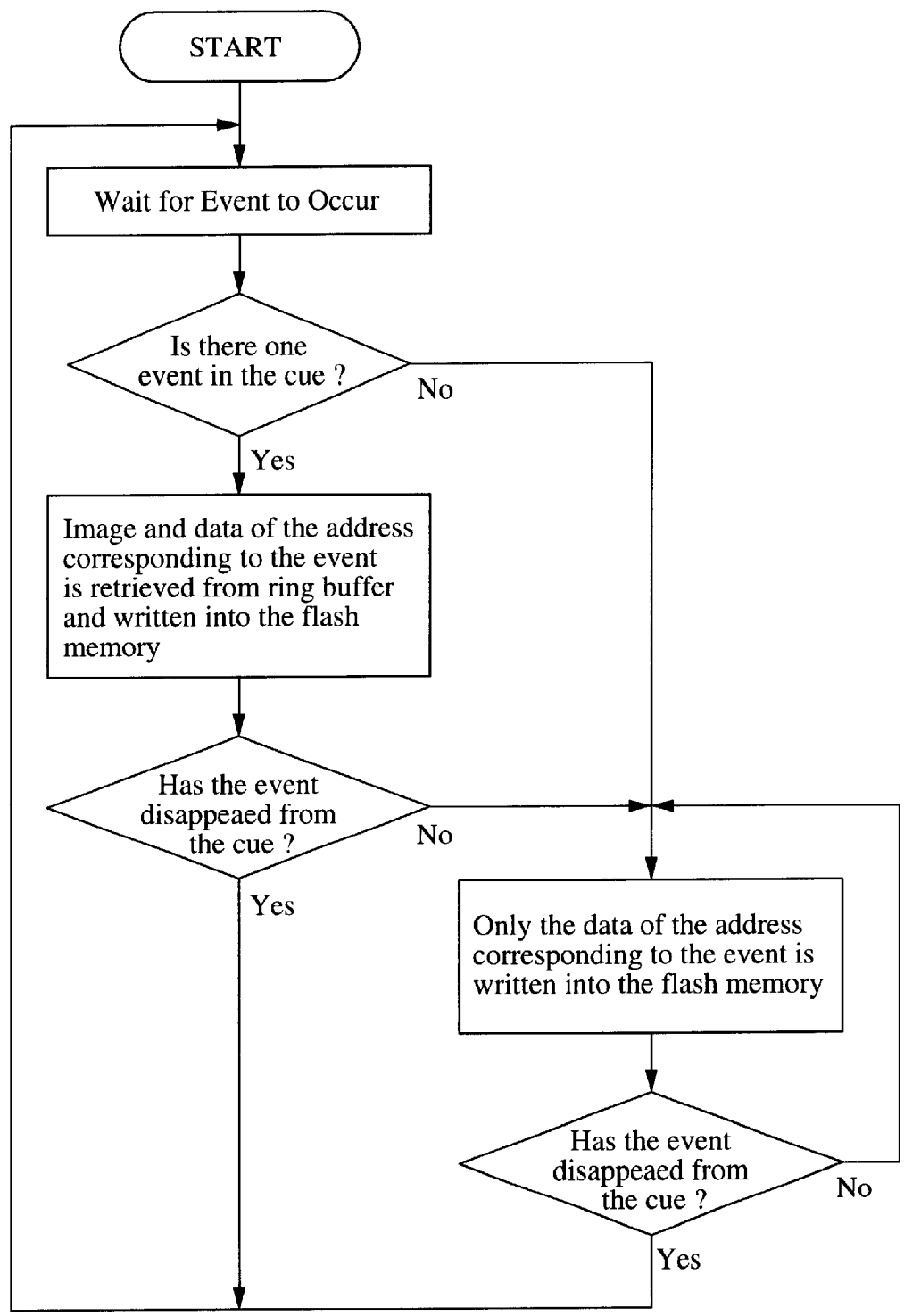
FIG. 9 is a flow chart for describing the operation of writing data into the storage device.

In this way, for the case where there is no image data, the item number of the recording execution event that occurred and each data at such time can be confirmed, and this makes it possible to analyze the cause of the occurrence of such recording execution event. Then, in order to carry out such process, the CPU 12a may be given a function to carry out the flow chart shown in FIG. 9. Namely, in the case where a flash memory write in operation is not being carried out at the time a recording execution event occurs (see A, D in FIG. 8), all the data is copied (stored) in the flash memory, and in the case where a flash memory write in operation is being carried out at the time a recording execution event occurs (see B, C in FIG. 8), data omitting the image data is stored.

Figure 10:
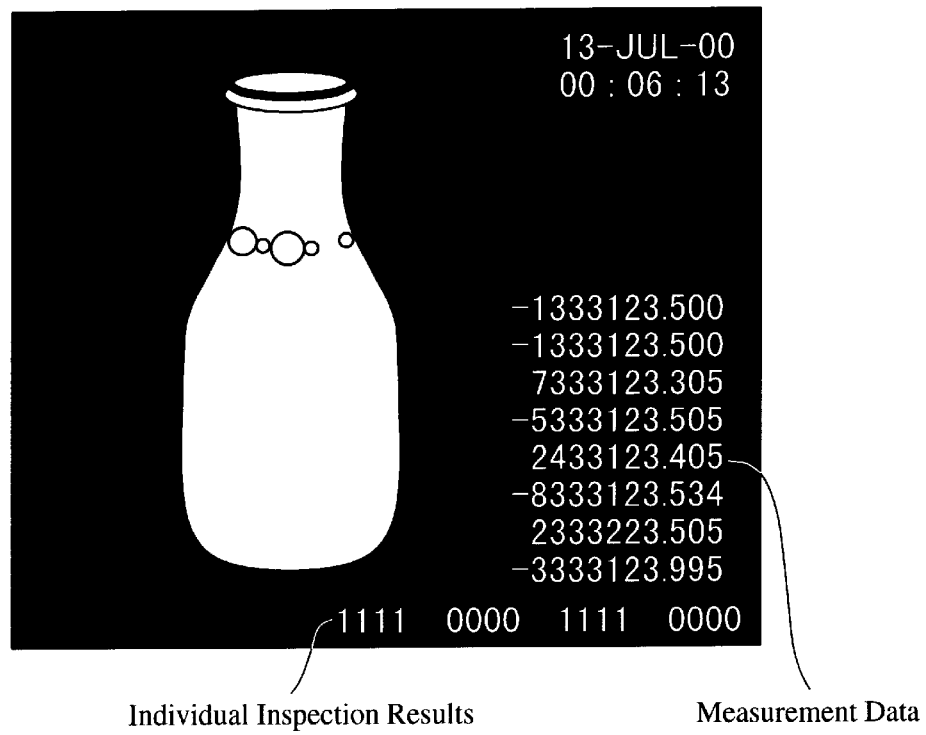
FIG. 10 shows an example of a playback image.
Figure 11:
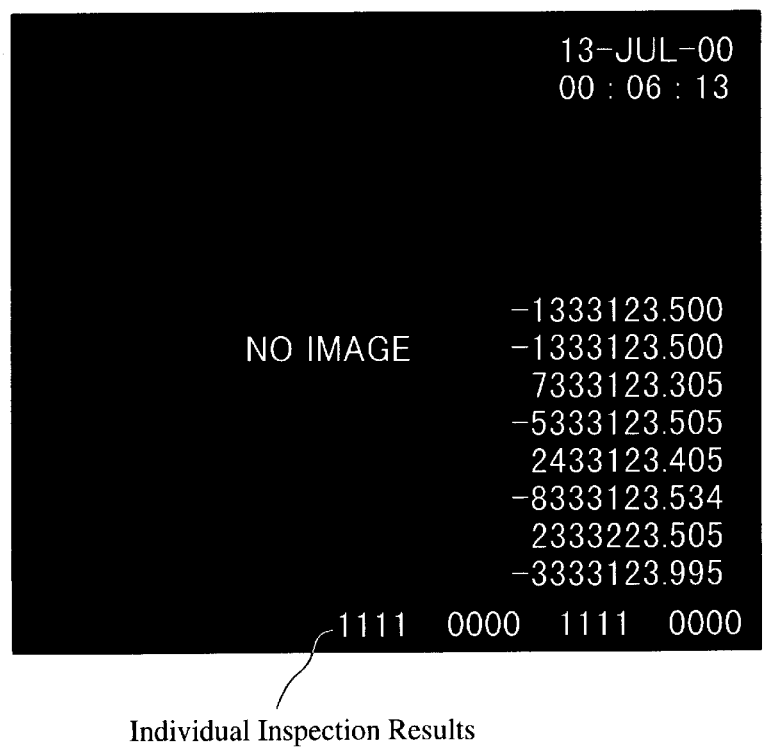
FIG. 11 shows another example of a playback image.

Then, in the case where data stored as described above is played back, for example, in the case where image data is also stored, the image data, measurement data and individual inspection results are outputted and displayed as shown in FIG. 10. On the other hand, in the case where an image is not recorded, the expression "NO IMAGE" is displayed in the image display region as shown in FIG. 11, and this display indicates that the inability to record an image was not due to a malfunction or the like.

Of course, in the case where the data is stored in a storage portion where a high-speed write in operation is possible for the main storage and the like, image data and all the data related thereto can be stored for all the recording execution events as shown in FIG. 12.

Next, the initialization for registering the relative position data that forms the reference for obtaining synchronization will be described. First, the production line is made to undergo actual operation, and then each type of data is obtained and written into the ring buffer RB. Then, during actual operations, a sample of a nonconforming article is imaged, a recording execution event is generated, and data (image, I/O, serial) for a prescribed time interval before and after such time is read out from the ring buffer RB.

Based on such read out data, the initialization screen shown in FIG. 13 is displayed. Namely, the NG signal, GATE signal and serial data (COM) are displayed in a top to bottom ordered arrangement. This display is carried out in a way that matches the times the image recording apparatus 12 acquired each data. Further, with regards to the image data, the acquisition timing of the fields are shown by the frames in the VD column. Namely, because these frames show the timing of video vertical synchronizing signals, there are 60 fields (30 frames) per second in NTSC. In other words, there is one image (field) stored in each frame. Further, the I/O data at the point in time where a recording execution event occurs is displayed as individual inspection results in the lower left portion of the screen.

In this regard, in order to show the occurrence position of the recording execution event, the field of the point in time where the event occurred is shown to be covered in white. Further, an area designating cursor K1 is a displayed as a vertical line on the screen. This area designating cursor K1 is moved left and right by VD frame units in a stepwise manner by controlling a console omitted from the drawings. Further, a square image display cursor K2 is formed on the right side of the area designating cursor K1 so as to overlap the VD column. This image display cursor K2 has a width that encloses two fields, and the combined image corresponding to the two fields enclosed by the image display cursor K2 is displayed as a single frame image G. Accordingly, if the area designating cursor K1 is moved by one field unit in a stepwise manner, because the image display cursor K2 is also moved thereby, the single frame image G created based on the two fields enclosed by the image display cursor K2 after such movement will be displayed.

Next, the initialization method used for this initialization screen will be described. First, the relative field number of the recording image is established in the manner described below.

Namely, the displayed area designating cursor K1 together with the image display cursor K2 are moved to the left end, for example. In accordance with this movement, the displayed frame image G is shifted one field at a time. Then, when such frame image G becomes an image frame displaying a nonconforming article, the position thereof is selected (This selection is carried out by pushing a prescribed button or the like on the console). This selected position forms the recording start position, and the field number from the reference position is calculated and established as the extracted start field position. Then, this extracted start field position is displayed as a number value (of the VD column) in the upper left portion of the initialization screen. For example, in the situation shown in FIG. 13, the value "4" is established as the shift field number from the reference position.

Next, the area designation cursor K1 (image display cursor K2) is moved to the right in the same manner to designate the end recording field (extracted termination position). This position can be selected by going back one field after reaching a field in which there is no display of a nonconforming article. Of course, the area of the fields having image data displaying nonconforming articles may be designated in this way, or when viewing the scope of such fields, designation may be carried out after establishing a fixed margin before and after such fields.

Further, the designation of the measurement data (COM) recording area is also established by moving the area designation cursor K1 to the left and right to select the start position and end position. At this time, in the present embodiment, the time the measurement data was acquired does not necessarily match the time when the recording execution event occurred, but it can be said that the measurement data acquisition time is close to the time the event occurred. Accordingly, the measurement data (COM) outputted closest to the reference field (covered in white) is assumed to be the measurement data of the recording object, and the area designation cursor K1 is moved to the head and end thereof to select the serial data recording head position and the serial data recording end position. Then, the relative times (in seconds) are calculated from the difference between the selected positions and the reference position, and these relative times are displayed as number values (of the COM column) on the left and right of the initialization screen.

In this way, because the image area for which recording is desired can be selected while displaying the timing chart and the actual acquired images, judgements can be carried out visually, and this makes it possible to achieve easy setup and accurate results.

Further, instead of a normal NTSC system (in which one frame is created by combining an odd numbered field and an even numbered field, wherein playback is achieved by carrying out frame-by-frame transmission one frame unit at a time), the image playback system in the present embodiment may be provided with a display system that carried out frame-by-frame transmission one field at a time.

Figure 14:
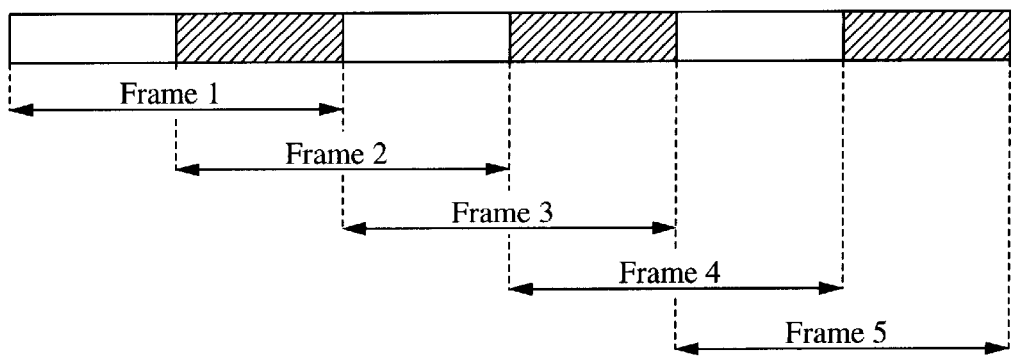
FIG. 14 is a diagram for describing the principle for playing back frames from the fields.

Namely, as shown in FIG. 14, the playing back of one frame using two fields is the same as the NTSC system, but the sending of frames for playback is carried out 0.5 frame units at a time (i.e., one field unit at a time). Namely, if the first frame is created based on the first and second fields, then the next frame will be played back based on the second and third fields (in the normal NTSC system, the next frame would be played back based on the third and fourth fields).

For example, in the case where it is possible for the image recording apparatus 12 to carry out recording by switching between images inputted from a plurality of cameras, regardless of the field interval where switching of the input images is carried out, it is possible to accurately acquire and playback the image at the point in time where such switching is carried out. Moreover, because the image is created based on two fields, there is no lowering of resolution in the vertical direction.

Figure 15:
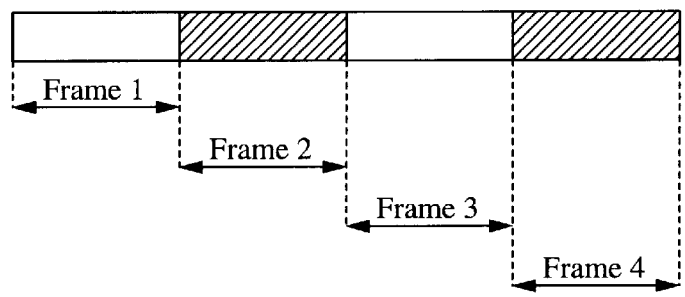
FIG. 15 is a diagram for describing the principle for playing back frames from the fields.

Further, the same results can be obtained even for a playback system like that shown in FIG. 15, where a prescribed supplemental process is carried out on a single field to play back a single frame. However, in this case, the vertical direction resolution becomes ½. In this regard, various types of processes may be utilized for such supplemental process, such as a process in which each line is doubled by expansion, or a process in which the lines before and after a line having no data are averaged to create a frame.

As described above, in the present invention, data (image data, inspection data corresponding to inspection results) for identifying the cause of the generation of a nonconforming article can be easily synchronized (connected) and stored at high speed based on relative position data for specific signals.

What is claimed is:

1. An image recording apparatus for recording image data of an inspection object and inspection data corresponding to inspection results outputted at their own respective timings from an inspection device which judges quality by an image recognition process, comprising:

a temporary storage portion for temporarily storing the image data and the inspection data;

storage means; and control means for synchronizing the image data and the inspection data and storing the synchronized image data and inspection data in the storage means based on relative position data from a prescribed signal sent from the inspection device, wherein the control means accesses the temporary storage portion to acquire previous data for at least the prescribed signal.

2. The image recording apparatus of claim 1, wherein the control means omits the recording of the image data and stores the inspection data in the storage means when a new recording execution event occurs while data is being stored in the storage means.

3. The image recording apparatus of claim 1, further comprising:

a display means;

wherein a timing chart showing at least the acquisition timing of the fields is displayed by the display means based on data stored in the temporary storage portion;

wherein a prescribed position of the displayed timing chart is designated, and image data based on the designated position is displayed on the display means independently or overlaid on the timing chart;

and wherein the control means is equipped with an initialization function to establish relative position data from the prescribed signal at the time when image data is being stored in the storage means based on the reception of an input which determines whether or not the displayed image should be stored in the storage means.

4. The image recording apparatus of claim 3, wherein the designation of the timing chart can be changed to field units.

5. The image recording apparatus of claim 2, further comprising:

a display means;

wherein a timing chart showing at least the acquisition timing of the fields is displayed by the display means based on data stored in the temporary storage portion;

wherein a prescribed position of the displayed timing chart is designated, and image data based on the designated position is displayed on the display means independently or overlaid on the timing chart;

and wherein the control means is equipped with an initialization function to establish relative position data from the prescribed signal at the time when image data is being stored in the storage means based on the reception of an input which determines whether or not the displayed image should be stored in the storage means.

6. An image recording apparatus for recording image data of an inspection object and inspection data corresponding to inspection results outputted at their own respective timings from an inspection device which judges quality by an image recognition process, comprising:

a temporary storage portion for temporarily storing the image data and the inspection data;

a storage device; and a control unit configured to synchronize the image data and the inspection data and store the synchronized image data and inspection data in the storage device based on relative position data from a prescribed signal sent from the inspection device, wherein the control unit accesses the temporary storage portion to acquire previous data for at least the prescribed signal.

* * * * *